US012618660B2

(12) United States Patent
Kight et al.

(10) Patent No.: US 12,618,660 B2
(45) Date of Patent: May 5, 2026

(54) IMPLANTABLE, STRETCHABLE SENSOR FOR CONTINUOUS BIOMECHANICAL MONITORING OF THE HEART

(71) Applicants: The Board of Trustees of the Leland Stanford Junior University Office of the General Counsel, Stanford, CA (US); Seoul National University, Seoul (KR)

(72) Inventors: Ali Kight, Stanford, CA (US); Mark R. Cutkosky, Palo Alto, CA (US); Doff McElhinney, Stanford, CA (US); Ileana Pirozzi, Albertson, NY (US); Xinyi Liang, Stanford, CA (US); Seraina Dual, Skärholmen (SE); Kyung Won Han, Seoul (KR)

(73) Assignees: The Board of Trustees of the Leland Stanford Junior University, Stanford, CA (US); Seoul National University, Seoul (KR)

( * ) Notice: Subject to any disclaimer, the term of this patent is extended or adjusted under 35 U.S.C. 154(b) by 292 days.

(21) Appl. No.: 18/432,591

(22) Filed: Feb. 5, 2024

(65) Prior Publication Data

US 2024/0263933 A1     Aug. 8, 2024

Related U.S. Application Data

(60) Provisional application No. 63/443,421, filed on Feb. 5, 2023.

(51) Int. Cl.
| | |
|---|---|
| *G01B 7/16* | (2006.01) |
| *A61B 5/00* | (2006.01) |
| *A61B 5/11* | (2006.01) |

(52) U.S. Cl.
CPC .............. *G01B 7/22* (2013.01); *A61B 5/1107* (2013.01); *A61B 5/6869* (2013.01); *A61B 2562/0261* (2013.01)

(58) Field of Classification Search
CPC ........ G01B 7/22; A61B 5/1107; A61B 5/6869
See application file for complete search history.

(56) References Cited

U.S. PATENT DOCUMENTS

| | | | |
|---|---|---|---|
| 7,082,330 B2 | 7/2006 | Stadler | |
| 8,121,687 B2 | 2/2012 | Jensen | |
| 9,095,284 B2 | 8/2015 | Cinbis | |
| 10,994,145 B2 | 5/2021 | Koop | |
| 2007/0163353 A1* | 7/2007 | Lec ...................... | A61B 5/6876 73/700 |

(Continued)

*Primary Examiner* — Daniel L Cerioni
(74) *Attorney, Agent, or Firm* — LUMEN PATENT FIRM

(57) ABSTRACT

A modular approach for strain sensors for large deformations is provided. The strain sensor separates the extension and signal transduction mechanisms using a soft, elastomeric transmission and a high-sensitivity microelectromechanical system (MEMS) transducer. By separating the transmission and transduction, they can be optimized independently for application-specific mechanical and electrical performance. The durability of the strain sensor was evaluated by conducting cyclic loading tests over one million cycles, and the results show negligible drift. Applications of the strain sensor are suitable for human health monitoring as for example an implantable cardiac strain sensor for measuring global longitudinal strain (GLS).

11 Claims, 11 Drawing Sheets

Barometric Pressure Sensor          Silicone

(56)                  References Cited

U.S. PATENT DOCUMENTS

2008/0255629 A1 *  10/2008  Jenson ................... A61N 1/056
                                                            607/19
2019/0150771 A1 *   5/2019  Jeong ....................... A61B 7/04
2019/0282173 A1 *   9/2019  Starr .................... A61B 5/6862
2023/0248249 A1 *   8/2023  Keidar ................ A61B 5/0215
                                                            600/486

* cited by examiner

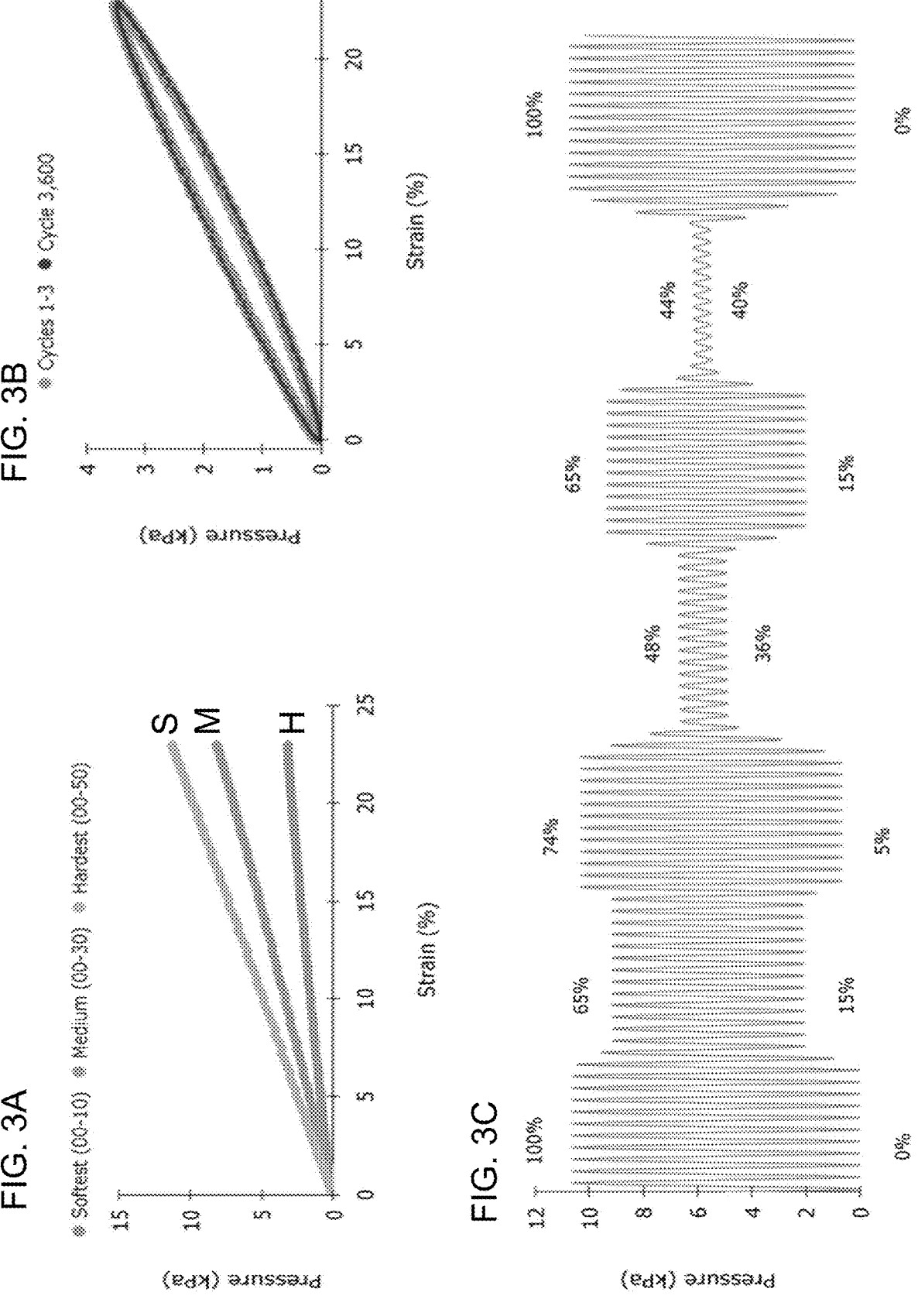

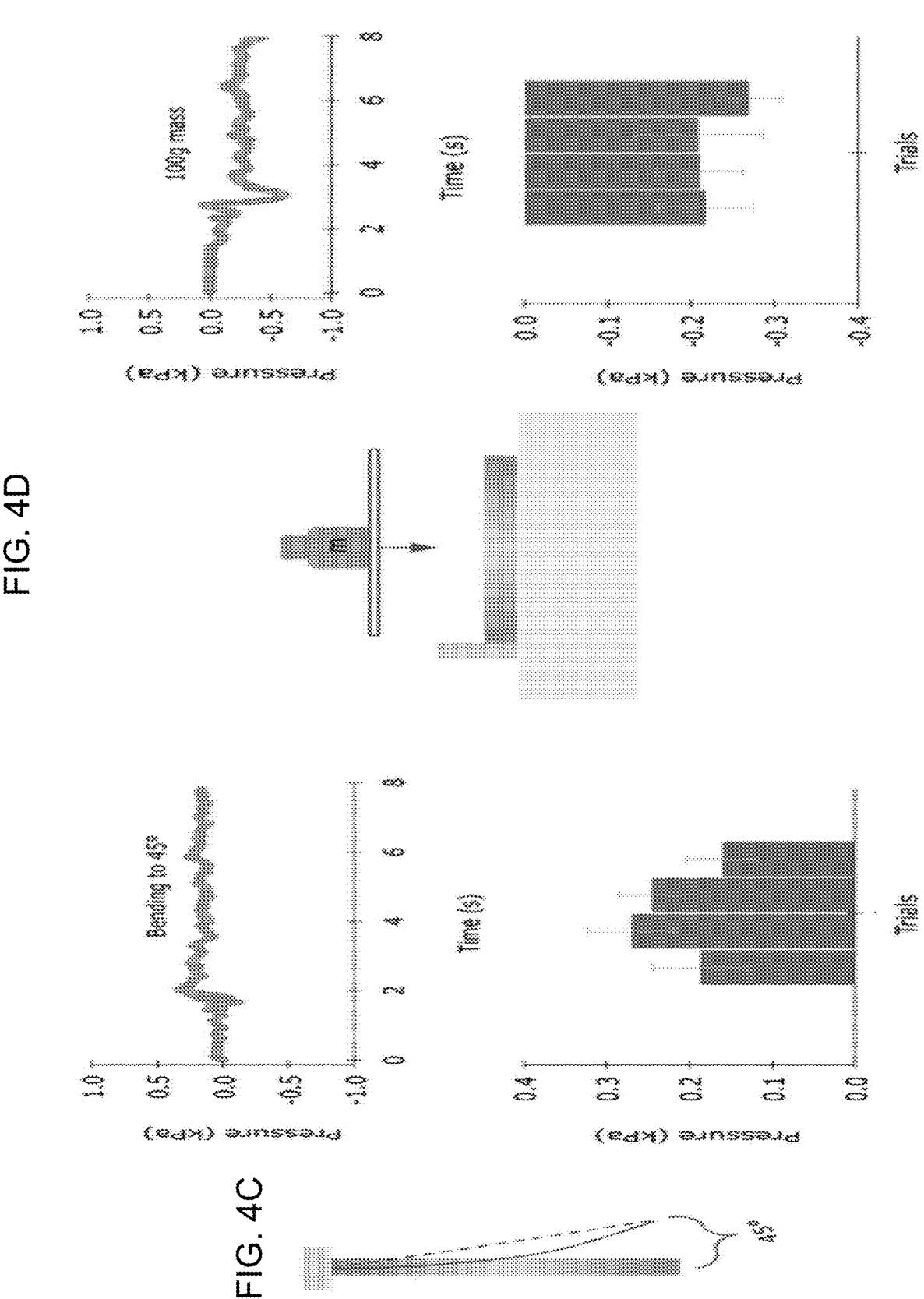

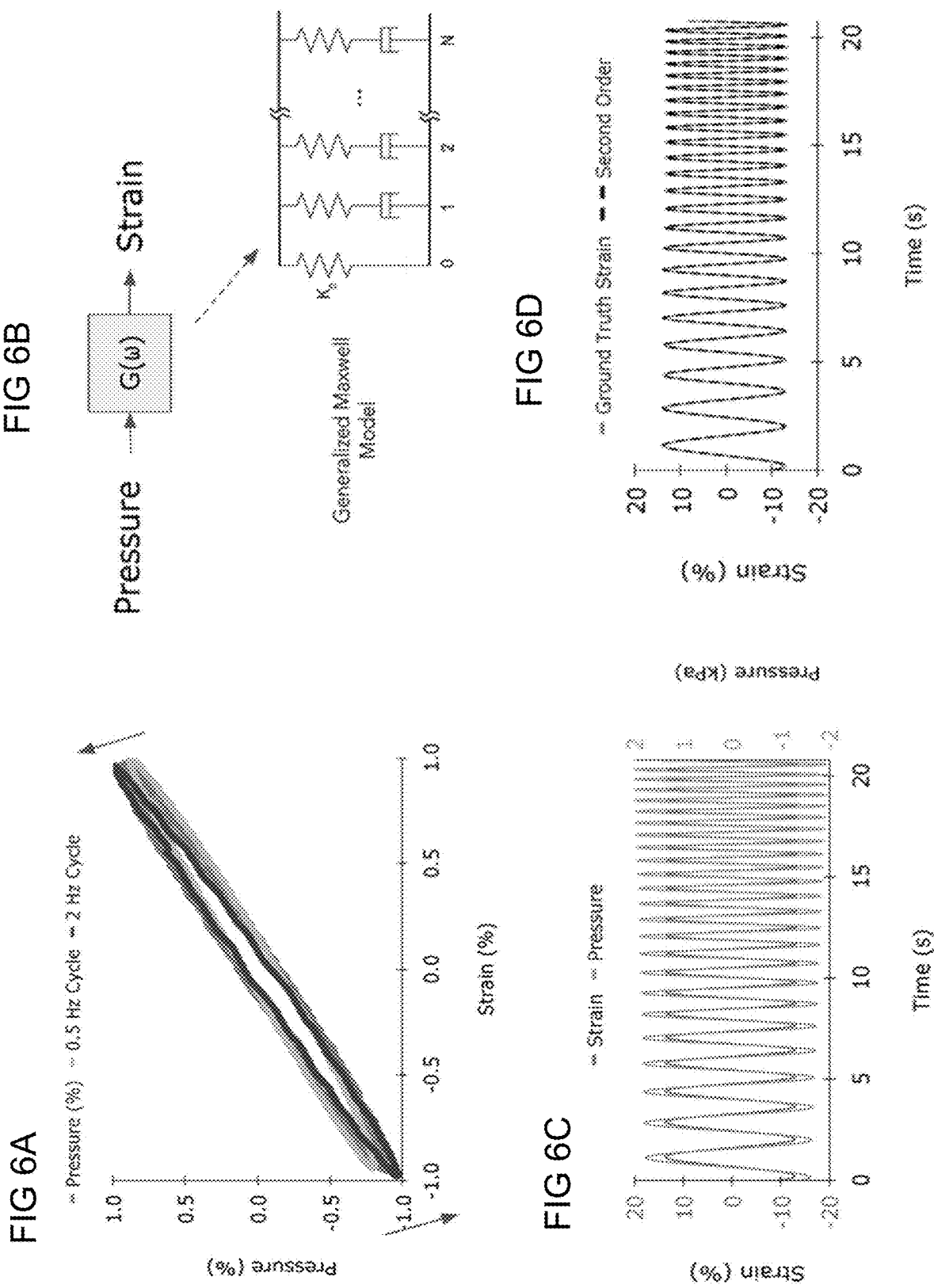

IMPLANTABLE, STRETCHABLE SENSOR FOR CONTINUOUS BIOMECHANICAL MONITORING OF THE HEART

CROSS-REFERENCE TO RELATED APPLICATIONS

This application claims priority from U.S. Provisional Patent Application 63/443,421 filed Feb. 5, 2023, which is incorporated herein by reference.

FIELD OF THE INVENTION

This invention relates to strain sensors.

BACKGROUND OF THE INVENTION

The ability to accurately sense large deformations of soft structures is becoming increasingly valuable in various fields, such as soft robotics, wearables, textiles, and implantable medical devices. Despite this interest, there have been few demonstrations of highly stretchable sensors that provide consistent and repeatable results over many cycles. Conventional strain sensors, such as semiconductor and piezoresistive gauges and microelectromechanical systems (MEMS), can be manufactured with high precision for robustness and are often used in industrial applications that require a high cycle life. Nevertheless, they are limited to measuring small strains and are typically manufactured out of rigid components, inhibiting their use in applications with large deformations and soft structures.

To overcome these limitations, recent research has focused on the development of highly-stretchable, large deformation strain sensors using novel materials, including, but not limited to, ionic hydrogels, conductive polymer composites, and liquid-metal-in-rubber. These methods can produce sensors with impressive signal-to-noise (SNR) ratios, but they often suffer from baseline conductive drift and unreliable interconnects between soft and rigid conductive components that limit their cyclic durability, with stable performance up to 60,000 cycles at best. Higher cycle life has been demonstrated but with evidence of sensor drift and changes in signal amplitude over time. Others have developed large deformation strain sensors by patterning inextensible conductors with rationally designed geometrical structures that impart stretchability (e.g. with a serpentine pattern), but this approach only permits stretch in a particular direction. Moreover, there is a large mismatch in bulk material stiffness between the conducting material and the soft substrate that can lead to undesirable local stress concentrations, particularly when stretch is perpendicular to the preferred direction of electrode patterning. This can inhibit the sensing of soft structures that stretch multidimensionally, which is often the case for human health and biomechanical monitoring applications. It is also worth noting that most of these sensors are intrinsically sensitive to pressure and bending, leading to difficulties in discerning between mechanical phenomena. Finally, others have attempted stretchable strain sensors that leverage the patterning or structural forming (e.g. wrinkling) of soft conductive materials, bypassing the limitation of mismatched mechanical properties but still leveraging the advantage of geometry-imparted stretchability for signal generation. However, the actual integration of such sensors remains challenging, and the development of robust, miniaturized signal amplification and readout circuitry and shielding mechanisms for practical applications of these sensors has yet to be demonstrated.

In these traditional strain sensing approaches, the transduction mechanism relies on the extension of the sensing unit, which results in a fundamental tradeoff between mechanical properties and electrical integrity under repeated large deformations.

SUMMARY OF THE INVENTION

Clinical research has established that imaging-derived measures of global longitudinal strain (GLS) of both the right and left ventricle are informative and predictive measures of cardiac health. Such functional monitoring can be particularly valuable in post-surgical settings, such as a post-mitral valve replacement, left ventricular assist device (LVAD) implantation, or heart transplantation. Nevertheless, echocardiographic imaging methods traditionally used to obtain GLS measurements require an expert clinician and measurements are person-dependent, inhibiting their use in remote settings; moreover, these measurements are intermittent rather than continuous and may miss critical changes in cardiac function. This challenge is relevant for doctors monitoring patients as well as drug and medical device companies trying to assess the effect of drugs and therapies in pre-clinical animal models.

To-date, no commercially available cardiac strain sensor exists. Direct cardiac mechanical monitoring has challenged the durability of conventional mechanical sensors due to the number of cycles of the beating heart (40M cycles/year) at high strains (15-20%).

Additionally, this particular application bears requirements for mechanical and material biocompatibility, given the soft nature of live heart muscle. Although many soft sensing technologies have been developed in a research setting, they lack the ability to operate over many cycles and suffer from integration challenges.

Embodiments of this invention use a decoupling mechanism, described below, to bypass the durability and integration challenges normally associated with stretchable sensors.

The sensor according to this invention uses a transmission and transducer pair to measure large strains. The transmission element couples the mechanical signal of interest to a robust, high-sensitivity transducer that converts the mechanical signal into an electrical signal. The transmission element can be visualized as a spring with some stiffness, while the transduction element can be visualized as a low-deformation normal force sensor that is mechanically attached to one end of the spring. As the spring is stretched, the normal force at the proximal end increases in proportion to the spring's stiffness, and that force is transduced into an electrical signal. By decoupling the transmission and transducer components, each can be optimized independently for its specific role in the system. The transmission can be designed to maximize its stretchability and mechanical consistency, without being concomitantly constrained with conductivity requirements. Meanwhile, the transducer can be optimized for efficient mechanical to electrical energy conversion, robust packaging, and integrated communication protocols, without simultaneous deformation requirements.

The working principle of this sensor allows for a broad choice of transmission and transduction elements. Given the requirements of a sensor that aims to be used for implantable applications, elements were selected that are biocompatible, robust, and miniaturizable. For the transduction element, the inventors chose a high-precision MEMS barometric pressure sensor (BMP384, Bosch Sensortec), having a transduction mechanism that relies on the deflection of a capacitive diaphragm. MEMs barometers are commercially available and industrially manufactured, ensuring high robustness and low noise. Further, these sensors come with integrated, on-board amplification and communication protocols, such as I2C, enabling a simple and compact readout system. For the transmission element, the inventors chose an elastomer with demonstrated biocompatibility, namely silicone, in the Shore 00 range which corresponds to a range of stiffnesses comparable to that of human tissue. Moreover, this material is isotropic and homogeneous, leading to directionally independent mechanical properties and minimal hysteresis compared to composite materials. Finally, the inventors designed the geometry of the elastomeric transmission element to be as small as possible but with a large enough cross-sectional area to completely cover the area of the pressure sensor (3 mm×3 mm) and span the height of a ventricle (5 cm), respectively.

In one example the invention can be characterized as a strain sensor. The strain sensor has a transmission element and a transduction element. The transmission element is an elongated homogeneous elastomer defining a width and a height of a cross-sectional area, a length (in range of 10 mm to 100 mm) and a Young's modulus (in range of 40 kPa to 500 kPa) of the elongated homogeneous elastomer. The elongated homogeneous elastomer can be made from silicone, polyurethane, sterene-isoprene-rubber, or natural rubber.

The transduction element has a MEMS transducer with integrated signal processing and digital communication. In one example, the MEMS transducer is a barometric pressure sensor with a capacitive diaphragm, where the capacitive diaphragm is attached to the cross-sectional area of an end of the transmission element. The attachment is such that the transmission element couples a mechanical signal of interest applied to an aspect of the transmission element to variations in stress onto the capacitive diaphragm, which is then converted into an electrical signal. The transmission element acts as a spring with a stiffness, and the transduction element acts as a deformation normal force sensor that is mechanically attached to the cross-sectional area of end of the transmission element, and when the spring stretches, the normal force at the cross-sectional area of end of the transmission element increases in proportion to the spring stiffness and that normal force is then transduced into the electrical signal.

In one example as a strain sensor for the heart, the transmission element is adapted in shape to confirm to a shape of a heart.

In another embodiment, multiple transduction elements can be organized in a three-dimensional pattern or a cube, and with that multiple transmission elements, where each of the capacitive diaphragms of the multiple transduction elements is attached to the cross-sectional area of the end of the respective transmission element of the multiple transmission elements. As such in another example as a strain sensor for the heart, the multiple transmission elements are adapted in shape to confirm to shapes of a heart.

As a variation, an arm can be cast to the three-dimensional pattern or the cube, where the arm is cast a more or less perpendicular fashion to the three-dimensional pattern or the cube.

In another variation, the transmission element can be cast with a material that is at least four times less stiff or substantially less stiff than a material of the transmission element. The material of the cast can be a silicone gel at least four times or substantially less stiff than the material of the transmission element. In another example, the material of the cast is a silicone, a polyurethane, or a material with a Shore 000 hardness.

Embodiments of the invention can be applied in the field of cardiovascular drug and therapy research, as a clinically deployable sensor for remote monitoring of patients, as sensors to use as an adjunct to other devices, such as LVADs, pacemakers, MitraClips/Annuloplasty Rings, or other applications where sensors of this kind can be useful.

BRIEF DESCRIPTION OF THE DRAWINGS

Noted it that the original drawings contain color, which for the purposes of this application have been converted to a grey scale. The reader is referred to the priority document for clarity or interpretation if needed and where applicable.

FIG. 1A is a depiction of the transduction and transmission elements. The right panel illustrates how they are mechanically assembled to couple signal with uniaxial strain. FIG. 1B is a MEMS barometer and soft silicone were chosen for the application. The transmission element is parameterized by the width, w, and height, h, of the cross-sectional area, the length, l, and Young's modulus, E, of the silicone. FIG. 1C is a rendering of the complete sensor assembly. FIG. 1D is a visualization of the sensor on the proposed application for measuring global longitudinal strain on the heart postoperatively.

FIGS. 3A-C show Static Sensor Characterization according to an exemplary embodiment of the invention. FIG. 3A is a characterization of sensors fabricated from various hardness elastomers, ranging from soft (Shore 00-10) to medium (Shore 00-30) to hard (Shore 00-50), demonstrating the tunability of sensor sensitivity. FIG. 3B is a response of the 00-10 sensor subjected to a 1 Hz sinusoidal controlled displacement. Cycles 1-4 are plotted in blue and Cycle 3,600 is plotted in black. The average standard deviation between each cycle is 0.013 kPa. FIG. 3A is a demonstration of 00-10 sensor displaced to various amplitudes ranging up to 100% strain. Numbers above and below the plot lines quantify the peak and trough strain values for each section.

FIGS. 4A-D show signal decoupling and sensitivity characterization according to an exemplary embodiment of the invention. FIG. 4A is the uncompensated signal (grey—410) quantifies the sensor's response to temperature changes, which appears linear ($R^2$=1). Changes in temperature can be subtracted through a linear calibration using the onboard temperature sensor, as demonstrated by the compensated signal (blue 420). FIG. 4B shows the transmission element being allowed to soak in water for 18 hours and then subjected to uniaxial cyclic loading. The graph demonstrates no change in output signal. FIG. 4C shows sensitivity to bending, evaluated by rotating the tip by 45 degrees. Four trials were conducted, yielding an average of 0.215 kPa and 0.046 kPa, respectively. The top graph illustrates a single trial over time, and the bottom graph displays each trial's mean and standard deviation with error bars. FIG. 4D shows sensitivity to normal pressure, evaluated by placing a 100 g weight on top of the sensor. Four trials were conducted, yielding an average and standard deviation of 0.230 kPa and 0.045 kPa, respectively. The top graph illustrates a single trial over time, and the bottom graph displays each trial's mean and standard deviation with error bars.

FIGS. 6A-D show sensor model for dynamic mapping according to an exemplary embodiment of the invention. FIG. 6A Graph of the normalized pressure vs. normalized strain response across frequencies ranging from 0.5-2 Hz. The orange loop represents the slowest cycling rate, while the black loop represents the fastest. FIG. 6AB is an illustration of how a transfer function, G(w), can be developed to map the input (pressure) to the output (strain). The model is parameterized by stiffness $K_0$ and number of Maxwell elements (0 to N). FIG. 6AC is an illustration of the training data for the model, with pressure (blue) and strain (orange) as input and output, respectively. FIG. 6D shows a comparison of the strain for ground truth and second order model.

FIG. 7A is a quantification and comparison of the error in predicted strain across various heart rates for zero, firs, second and third order models, displayed as percent strain and percent error of strain magnitude. FIGS. 7B-C offer different visualizations of results for the 90 beats-per-minute case.

FIG. 8A Left: picture of the ventricular heart phantom benchtop setup. Middle: Illustration of phantom cross section with sensor demonstrating shear stress induced in the transmission element upon inflation. Right: Placement of hydrogel between the sensor and phantom reduces friction, eliminating shear and allowing for uniaxial stretch in the transmission. FIG. 8A shows a sensor signal for 70 mL inflation and deflation of the phantom with and without the hydrogel present.

DETAILED DESCRIPTION

The present invention provides embodiments describing a large deformation strain sensing paradigm that decouples extension and signal transduction into separate components using a mechanical transmission system. Specifically, this approach leverages a non-conductive, soft elastomeric transmission that relays a mechanical signal to a high-sensitivity, robust MEMS transducer. The elastomeric transmission element converts high strain, low stress mechanical energy to low strain, moderate stress on the MEMS transducer, which converts the mechanical energy into electrical energy for communication. Because the transmission element does not have to conduct electricity, it can be optimized solely with respect to its mechanical properties. This allows for the electrical components to be compact and enables the use of mass-produced, highly-engineered electrical transducers with on-board amplification and communication systems. For some of the same reasons, MEMs transducers have been used in tactile and force sensing applications, such as robotic surgical grippers. Overall, this approach offers improved performance and integration capabilities for practical applications that involve soft materials and large strains.

In the following sections, the sensing principle is described in detail and demonstrate how this decoupling of mechanisms provides several advantages, such as design tunability, selective sensitivity, and high SNR. It also leads to comparatively high durability, making the sensor suitable for demanding applications that require millions of cycles. Given the sensor's high mechanical lifetime under large deformation in particular, the inventors investigated its application as an implantable cardiac strain sensor, where it must withstand millions of heartbeats at high strains but provide robust and continuous communication.

Sensor Concept and Application

Sensing Principle

Figure 1:
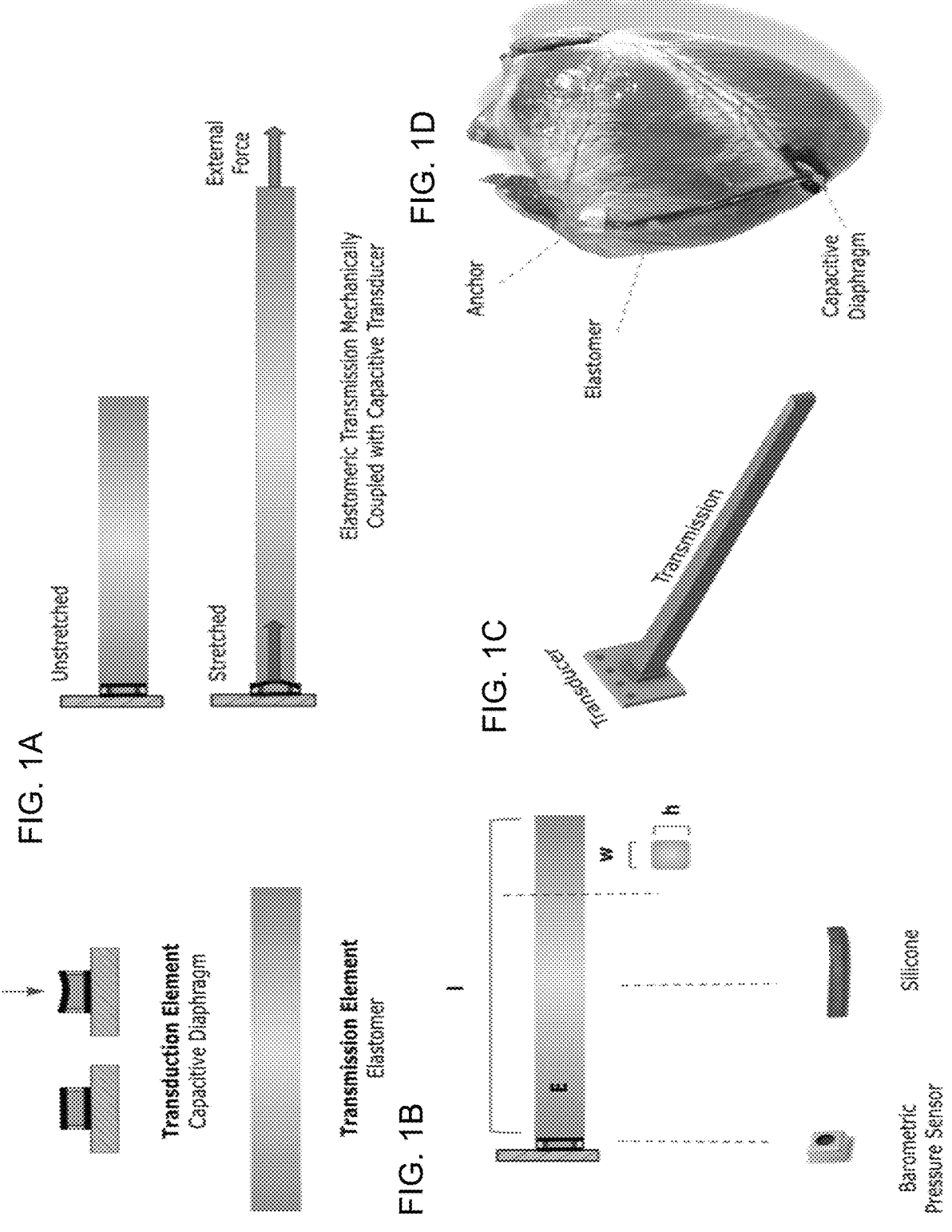
FIGS. 1A-D show the sensing concept according to an exemplary embodiment of the invention.

The sensor uses a transmission and transducer pair to measure large strains (FIGS. 1A-D). The transmission element couples the mechanical signal of interest to a robust, high-sensitivity transducer that converts the mechanical signal into an electrical signal (FIGS. 1A-C). The transmission element can be visualized as a spring with some stiffness, while the transduction element can be visualized as a low-deformation normal force sensor that is mechanically attached to one end of the spring (FIG. 1A, right). As the spring is stretched, the normal force at the proximal end increases in proportion to the spring's stiffness, and that force is transduced into an electrical signal. By decoupling the transmission and transducer components, each can be optimized independently for its specific role in the system. The transmission can be designed to maximize its stretchability and mechanical consistency, without being concomitantly constrained with conductivity requirements. Meanwhile, the transducer can be optimized for efficient mechanical to electrical energy conversion, robust packaging, and integrated communication protocols, without simultaneous deformation requirements.

Application

The sensor can find a range of applications spanning soft robotics to implantable devices. The inventors believe the latter field has encountered the greatest challenges with respect to durability, complicated by the requirement for material biocompatibility given the intimate interaction with human tissues. Thus, they have identified human health as the segment with the highest need for technical solutions. In response to this clinical challenge, the inventors demonstrated the design and assessment of this strain sensing paradigm in the context of a cardiovascular application, namely implantable cardiac functional monitoring. Direct cardiac mechanical monitoring has challenged the durability of conventional mechanical sensors due to the number of cycles of the beating heart (40M cycles/year) at high strains (15-20%). Additionally, this particular application bears requirements for mechanical and material biocompatibility, given the soft nature of live heart muscle. Nevertheless, direct mechanical metrics of heart function are known to be clinically useful in predicting and monitoring the state of cardiac health, particularly in patients with known cardiac disease. Clinical research has established that imaging-derived measures of global longitudinal strain (GLS) of both the right and left ventricle are informative and predictive measures of cardiac health. Such functional monitoring can be particularly valuable in post-surgical settings, such as a post-mitral valve replacement, left ventricular assist device (LVAD) implantation, or heart transplantation. Nevertheless, echocardiographic imaging methods traditionally used to obtain GLS measurements require an expert clinician and measurements are person-dependent, inhibiting their use in remote settings; moreover, these measurements are intermittent rather than continuous and may miss critical changes in cardiac function. The development of a robust and accurate compliant strain sensor that can be implanted during the time of surgery and continuously monitor cardiac GLS after the patient leaves the hospital would enable physicians to monitor patients' health remotely, optimize treatment, and predict adverse outcomes in real-time. A visualization of the proposed embodiment (on the right ventricle, for example) is shown in FIG. 1D. Towards the development of a sensor that can be practically implemented, the inventors demonstrated the sensor's ability to perform under the unique and demanding constraints of such an application, listed here:

1. Soft: comparable to the stiffness of native heart tissue (50 kPa [24]).
2. Durable: consistent signal over at least a million cycles (corresponding to about 11 124 days at 60 beats per minute).
3. Selectively Sensitive: insensitive to non-uniaxial strain signals that might occur, such as bending from the heart's torsion or pressure from external organs.
4. Conformable: consistent signal on a dynamic and compliant curved surface.
5. Extensible: achievable strains of at least 20% with a corresponding stable and predictable signal.
6. Dynamic: consistent and accurate signal at various heart rates and under dynamic load profiles that contain various frequency components.
7. Biocompatible: made of non-toxic materials that can be implanted with minimal inflammatory response from the tissue.

Sensor Design and Fabrication

Application Specific Design Selections

The working principle of this sensor allows for a broad choice of transmission and transduction elements. Given the requirements of a sensor that aims to be used for implantable applications, elements were selected that are biocompatible, robust, and miniaturizable. For the transduction element, the inventors chose a high-precision MEMS barometric pressure sensor (BMP384, Bosch Sensortec), having a transduction mechanism that relies on the deflection of a capacitive diaphragm. This selection provides a tactile sensor that uses elastomeric potting to transform a MEMS barometer into a compliant force sensor. MEMs barometers are commercially available and industrially manufactured, ensuring high robustness and low noise. Further, these sensors come with integrated, on-board amplification and communication protocols, such as I2C, enabling a simple and compact readout system. For the transmission element, the inventors chose an elastomer with demonstrated biocompatibility, namely silicone (Ecoflex, Smooth-On), in the Shore 00 range which corresponds to a range of stiffnesses comparable to that of human tissue. Moreover, this material is isotropic and homogeneous, leading to directionally independent mechanical properties and minimal hysteresis compared to composite materials. Finally, the inventors designed the geometry of the elastomeric transmission element to be as small as possible but with a large enough cross-sectional area (w and l) and length (l) to completely cover the area of the pressure sensor (3 mm×3 mm) and span the height of a ventricle (5 cm), respectively.

Sensor Fabrication

Figure 2:
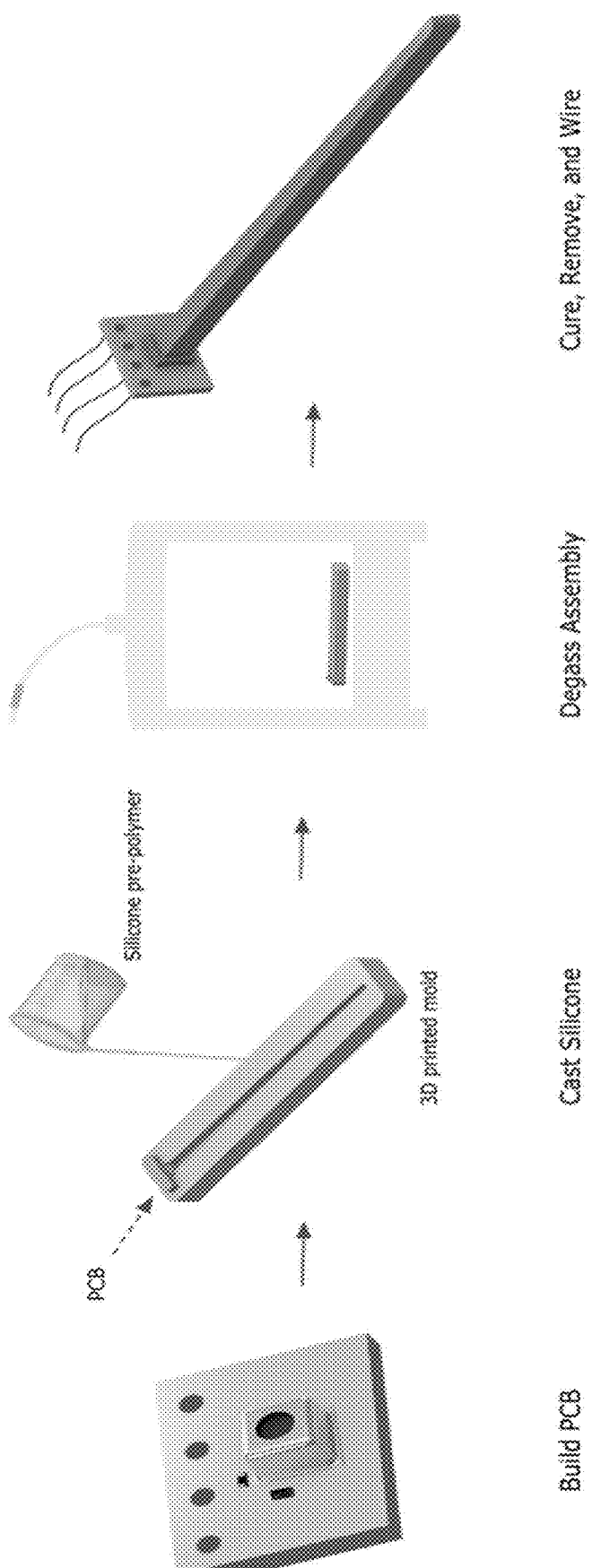
FIG. 2 shows the sensor fabrication according to an exemplary embodiment of the invention. The sensor is fabricated in a quick, facile manner. The PCB is potted with silicone of the chosen dimensions programmed into a negative 3D printed mold. The entire assembly is degassed and then left to cure. Wires are then soldered for $I^2C$ communication.

The sensor can be fabricated in four steps, as illustrated in FIG. 2. First, a printed circuit board (PCB) was designed and manufactured (OSH Park, Oregon, USA), mounting the pressure sensor and ancillary electrical components. A custom 3D printed mold was designed and manufactured to hold the PCB in place and provide a form to cast the silicone transmission element so as to completely encapsulate the pressure sensor. To optimize the sensitivity of the sensor, the entire assembly was degassed, removing the air inside the MEMS chip and allowing the silicone prepolymer to completely infiltrate the protective casing and bond directly to the capacitive membrane of the pressure sensor. The assembly was left to cure, and once the sensor was removed, wires were soldered for I2C communication to an off-board ATmega microcontroller (Arduino, USA). The entire process, excluding the time required to manufacture the PCB and print the mold, takes about thirty minutes and is largely dependent on the cure time of the polymer. Additionally, the entire assembly costs less than fifty US dollars.

Sensor Characterization

Quasi-Static Characterization

To confirm the sensing principle, the sensor was characterized in a quasi-static condition at a consistent and controlled frequency of 1 Hz, corresponding to a typical resting heart rate of 60 beats per minute (bpm). The sensor was stretched uniaxially using a dual-mode muscle lever with programmed displacement control (Aurora Scientific 309C). Multiple sensors were fabricated out of elastomers of various hardnesses for comparative analysis. Because the transduction element is a pressure transducer, the signal is reported in pressure (kPa). Further, because the transmission element pulls the diaphragm away (see FIG. 1B), a tensile strain results in a pressure decrease from baseline (atmospheric pressure); however, FIGS. 3A-C reports absolute changes in pressure. Uniaxial testing results in FIG. 3A demonstrate that strain and pressure are linearly correlated (R2=1 for all hardnesses) and that the sensitivity of the signal can be increased by increasing the hardness, or correspondingly the Young's Modulus, of the transmission element. Overall, there is a general tradeoff between stiffness and sensitivity. This makes intuitive sense, as the stress on the capacitive diaphragm will increase in proportion to the stiffness of the elastomeric element.

The sensor displays an impressive signal-to-noise ratio (SNR), even with the softest elastomer. Specifically, the sensor composed of the 00-10 shore hardness elastomer has a sensitivity of 136 Pa per percent strain, and the transducer has an unfiltered RMS noise of 1.2 Pa, yielding an SNR of over 100. As the Shore hardness of 00-10 (empirically determined to be 7 kPa) is softer than cardiac tissue yet still provides sufficient signal, the inventors chose to continue analysis with this.

FIG. 3B illustrates sensor response under cyclic loading. Cycles 1,2,3, and 3,600 were comparatively evaluated to assess signal consistency and the raw data is plotted, illustrating the spread of the sensor readings. The average standard deviation between cycles was 0.013 kPa. The sensor displays moderate but consistent hysteresis. This result is expected given that silicone is a viscoelastic material. FIG. 3C shows the sensor signal under an arbitrary range of sinusoidal strain amplitudes.

Decoupling Undesirable Signals

In uncontrolled settings, it is likely that a sensor will experience environmental changes and mechanical loads that could influence the signal and confound sensor readings. This is particularly true in the proposed application of a cardiac GLS sensor. Even though the sensor should only provide a signal for unidimensional strain in the longitudinal direction, the heart creates a challenging environment. Upon implantation, the sensor will be submerged in a primarily aqueous environment, and, although the range of body temperature is fairly limited (36-37 Degrees Celsius), previous analysis of a silicone-potted MEMS sensor has demonstrated significant temperature sensitivity. The sensor's responses to these environmental factors were evaluated, and results are depicted in FIG. 4A-B.

Figures 4A, 4B:
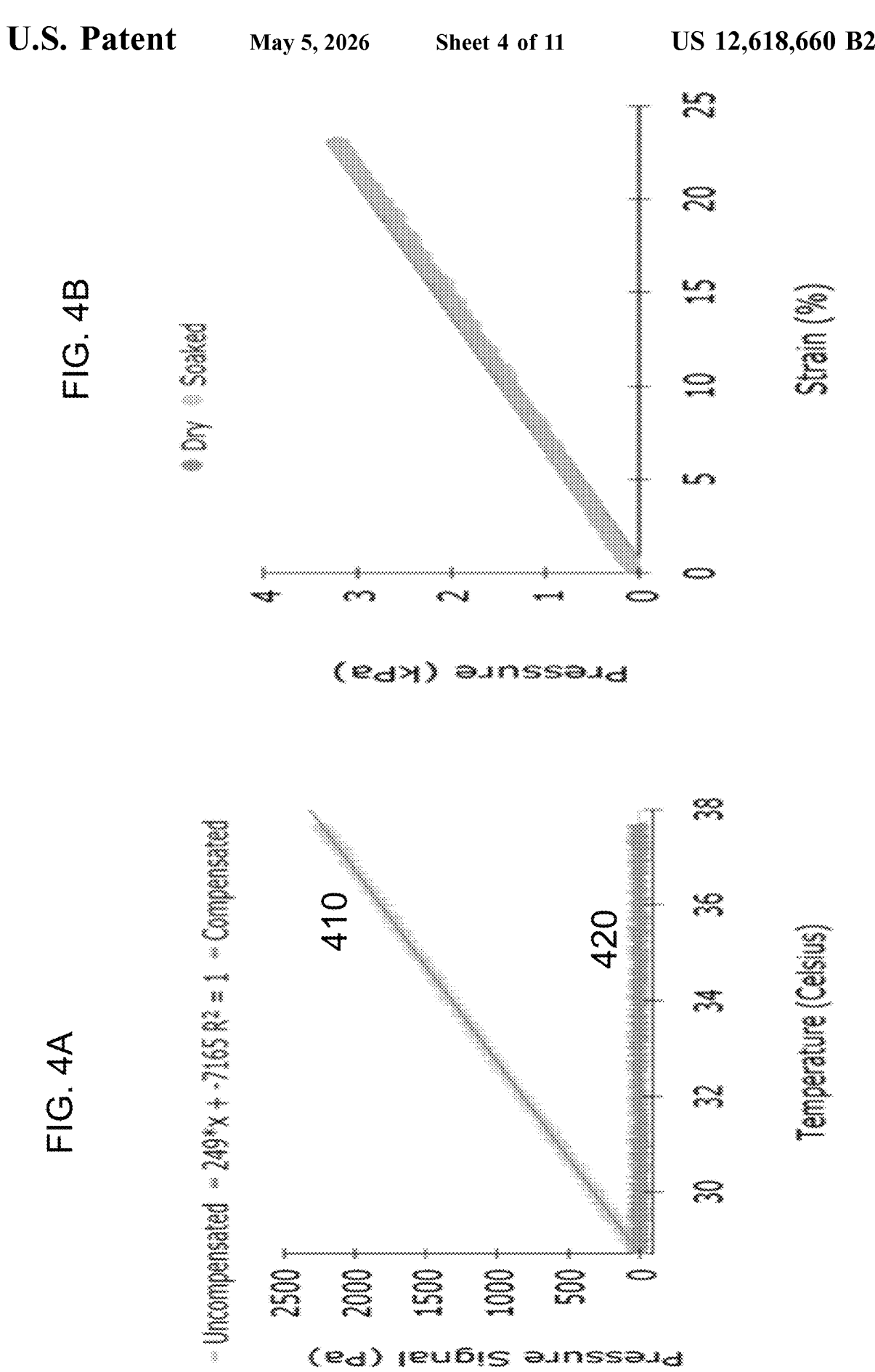

FIG. 4A illustrates the raw response of the static sensor assembly being heated across a range of physiological temperatures. The relationship between pressure and temperature appears linear (R2=1). The result matches well with previous work that also observed a linear relationship between sensor readings and pressure when temperature was increased, and in this work it was hypothesized that the bonding of silicone to the internal silicon diaphragm of the MEMS likely influences the composite thermal coefficient of expansion and could partially account for the observed effect. Sensor drift due to temperature can be easily compensated for with the onboard temperature sensor of the BMP384. To evaluate the sensor in an aqueous environment, the silicone transmission was left submerged in water over 18 hours and subsequently tested. FIG. 4B plots the sensor response for both the dry and submerged sensors, indicating that water has little effect on the mechanical properties of the silicone.

In the intended application, the sensor could experience contact pressure from nearby organs and experience non-longitudinal loading, primarily associated with bending, as the heart twists during contraction. The sensor's response to these scenarios was evaluated. The sensor was subjected to bending up to 45 degrees, as illustrated in FIG. 4C. The sensor was bonded to a glass plate in two places, at the PCB end and the distal end of the transmission, and the distal end was displaced along an arc of radius equal to the sensor's length. The bending test was conducted four times, and FIG. 4C (top) displays a representative trace. The sensor was held at 45 degrees for approximately 3 seconds; averages and standard deviations are illustrated in the bottom graph of FIG. 4C. On average, bending resulted in a 0.215 kPa signal response with a standard deviation of 0.046 kPa. This displacement-driven loading condition is dominated by bending but may include small amounts of stretch, compression, and/or shear. Hence, the inventors expected a small change in the transducer signal, as confirmed in the plot.

To evaluate the sensor's response to external pressure, a 100-gram weight was placed on the silicone transmission using a glass slide to distribute the load. This pressure test was conducted four times, and FIG. 4D (top) displays a representative trace. The weight was placed on the sensor for approximately 3 seconds for each trial; averages and standard deviations are illustrated in FIG. 4D bottom graph. On average, the added weight resulted in a −0.230 kPa signal response with a standard deviation of 0.045 kPa. The loading condition may produce a small amount of stretch near the proximal end due to the deformation caused by the edge of the glass slide, evidenced by a slight change in transducer signal in FIG. 4D.

Durability

Figure 5:
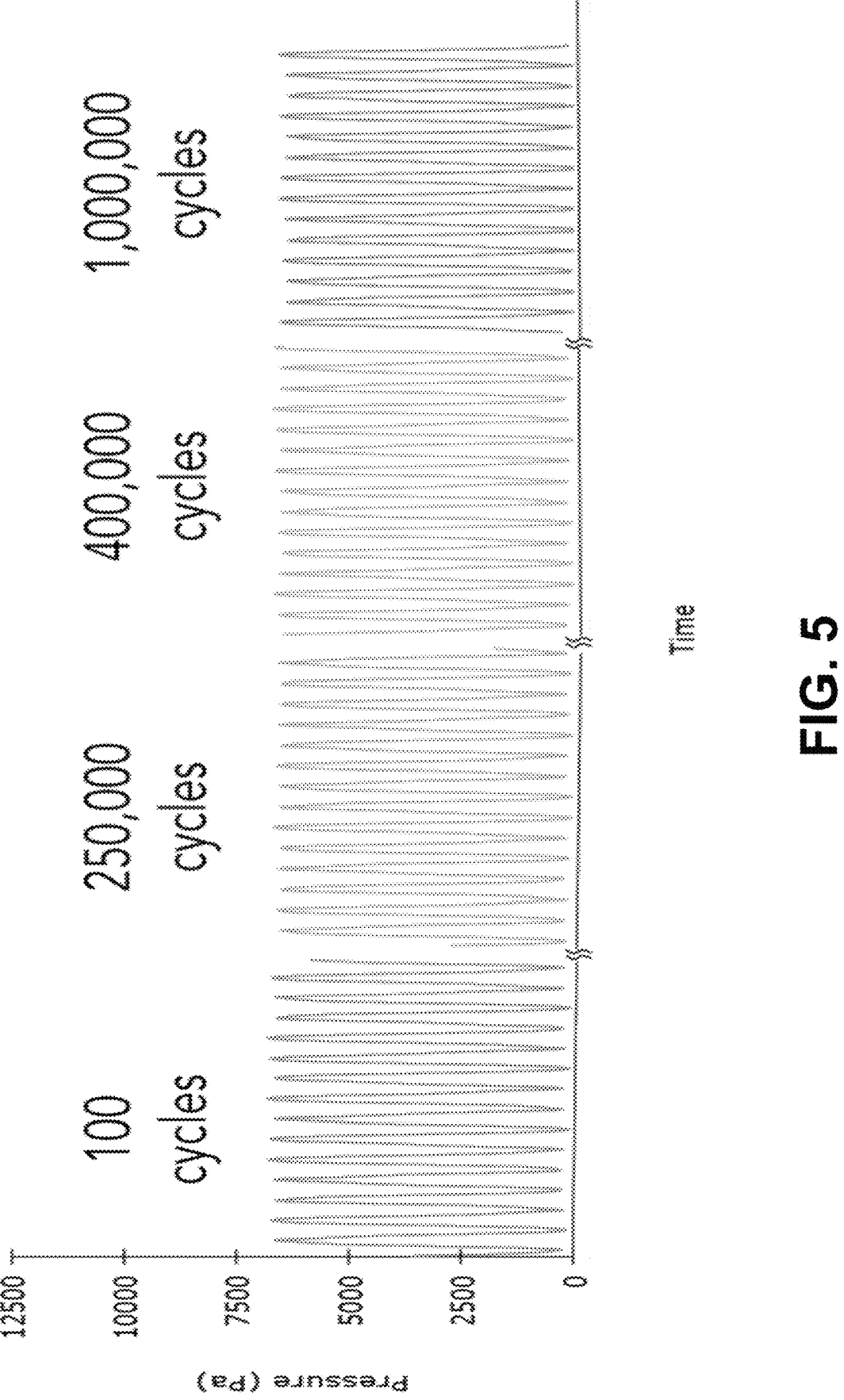
FIG. 5 shows a durability analysis according to an exemplary embodiment of the invention. Sensor durability was investigated through cyclic loading at 20 Hz for one million cycles. The output signal shows negligible drift.

The inventors investigated the durability of the sensor under long-term cyclic strain. Specifically, the sensor was loaded with a sinusoidal displacement of 30% strain at 20 Hz, corresponding to 1.5 cm of extension. FIG. 5 illustrates sensor response over 1,000,000 cycles. There is a slight baseline drift from cycle 100 to cycle 1,000,000 of about 109 Pa. This could be attributed to a change in temperature that is smaller than the manufacturer-defined absolute accuracy of the onboard MEMS pressure sensor (0.65 degrees Celsius). Given our empirically defined calibration (FIGS. 4A-C) of 249 Pa per degree Celsius, a change in 0.44 degrees Celsius could account for such a change in pressure. Signal drift that occurs in conventional stretchable sensors during cyclic mechanical loading can be attributed to many factors, a main one being the rearrangement of conductive particles in the soft, polymeric matrix, which can result in baseline resistive drift and even complete loss of conductivity. Selection of a pure, non-conductive polymer as the deforming element eliminates the risk of signal drift due to particle migration. Moreover, elastomers of a single polymer network exhibit less hysteresis and are generally more elastic than filled polymers which may reduce mechanical creep compared to composite elastomers. Finally, the integrated electronics of the MEMS pressure chip reduce the risk of mechanical and electrical interconnect instability, improving the cycle-life of the sensor. These features likely contribute to the enhanced signal stability and drift-free nature of the sensor.

Dynamic Characterization

Although a quasi-static characterization is useful for demonstrating the basic function of the sensing principle, practical applications of medical and in-body strain sensors involve varying frequencies. The sensor was sinusoidally strained across a range of physiologically relevant frequencies, ranging from 0.5-2 Hz. FIG. 6A plots sensor signal as a function of strain, demonstrating a slight frequency dependence of the sensor that cannot be captured by a quasi-static characterization. Not only is there a hysteretic component to the response, but the sensitivity, or slope, of the signal increases by as much as 25% at the highest swept frequency. This is illustrated by the pressure-strain response rotating counter-clockwise about the origin. Because the pressure signal is directly linked to the mechanical behavior of the transmission element, this response can be attributed to the time-dependent viscoelastic nature of the silicone. Without a proper compensation or mapping algorithm, it would be impossible to differentiate between a change in frequency at a constant amplitude and an increase in strain amplitude at the same frequency. This is important for cardiac applications as heart rate can vary over the course of minutes; moreover, a single heart beat can contain high strain-rate components, as total systolic contraction occurs over a fraction of the whole heartbeat.

The use of model-based transfer functions has been demonstrated to effectively compensate for hysteresis and strain-rate dependent material behavior in elastomeric sensors. To enable dynamic mapping of sensor pressure signal to ground-truth strain, a transfer function based on a multi-element rheological model that represents dynamic stiffness of an elastomeric transmission element is constructed. Rheological models are typically composed of both spring and damper elements to represent the elastic and viscous contributions of a viscoelastic material, respectively. Specifically, the inventors choose a standard generalized Maxwell model (GMM) to represent our system, depicted in FIG. 6B. The dynamic stiffness, or stress over strain, of a GMM can be modeled in the frequency domain as follows:

$$Z(w) = K_0 + \hat{A}^{\sum^N \frac{jwK_iC_i}{K_i + jwK_iC_i}} (1)_{i=1}$$

where $K_0$ is the static stiffness and $K_i$ and $C_i$ are the stiffness and damping values for the Maxwell element i, respectively. This can be converted into the equivalent pole-zero formulation:

$$Z(w) = K_0, \prod^N \frac{1 + (jw/w_{z,i})}{1 + (jw/w_{p,i})} (2)_{i=1}$$

However, pressure will be considered the input to the system and mapped to strain, so the transfer function can be thought of as a model for dynamic compliance as opposed to stiffness. Therefore, the transfer function G(w) is defined as $$G(w) = \frac{1}{Z(w)} = \frac{1}{K_0} \prod^N \frac{1 + (jw/w_{p,i})}{1 + (jw/w_{z,i})} (3)_{i=1}$$

Thus, the transfer function variables that can be tuned are the number of zero-pole pairs (N), each of which represent a single Maxwell element, and the values of $w_{z,i}$ and $w_{p,i}$ in (2), which are related to the stiffness and damping of the system. Using readily available MATLAB functions such as tfest( ), the inventors fit a transfer function to map the pressure output to the ground-truth frequency sweep for a varying number of Maxwell elements (N=1, 2, and 3). The raw data was modified slightly to facilitate the model fitting process. Specifically, the raw pressure waveform from the frequency sweep was converted from Pa to kPa and multiplied by −1, given that pressure decreases as strain increases, and both signals were detrended. A visualization of the modified empirical data is presented in FIG. 6C. A zero-order mapping refers to the linear calibration made in the quasi-static characterization (FIG. 3A).

TABLE 1

Transfer Function Parameters - Gain ($1/K_0$), Zeros, and Poles, are reported for each model order fitting (N = 0, 1, 2, and 3) and % Error of the model's performance on the validation set is reported as a percent of the total strain signal amplitude.

| Elements (N) | $1/K_0$ | Zeros | Poles | % Error |
|---|---|---|---|---|
| 0 | 7.35 | n/a | n/a | 5.48 |
| 1 | 6.32 | −7.26 | −5,32 | 2.25 |
| 2 | 6.17 | −11.26, −1.75 | −8.97, −1.43 | 1.76 |
| 3 | 7.14 | $-7 \times 10^6$, −9.33, −1.53 | $-6 \times 10^6$, −11.8, −1.85 | 1.80 |

The MATLAB function tf2zp( ) was used to determine the values for the gain, poles, and zeros from the transfer function obtained from tfest( ), which outputs a ratio of polynomials. The gain is equal to the inverse of stiffness $K_0$, following from (3), with units of (% Strain)/kPa. Table 1 presents the identified values for each Maxwell model order and their respective errors on the validation data. The errors suggest that two Maxwell elements are sufficient to comprehensively capture the viscoelastic transmission response. The second order model response is plotted in FIG. 6D overlaid on the input data. Overall, the second order TF mapping demonstrates excellent hysteresis and frequency-dependent stiffness compensation to yield predicted strain values that map to ground-truth with an average error of 0.3% strain, or 1.76% error. Although the gain, poles, and zeros are sufficient to uniquely describe the system, a mathematical relationship between the zeros and poles and the constitutive parameters $K_i$ and $C_i$ in eq.(1) has been described before.

Application-Specific Testing

Strain Sensing of a Realistic Heartbeat

To validate the models on physiologically realistic test data, the sensor was stretched at a strain-time profile that represented true cardiac contraction. The strain-time profile was gathered from literature data and used to program muscle lever displacement. The sensor was strained according to this displacement profile at 60, 90, and 120 beats per minute (bpm).

Figures 7A, 7B, 7C:
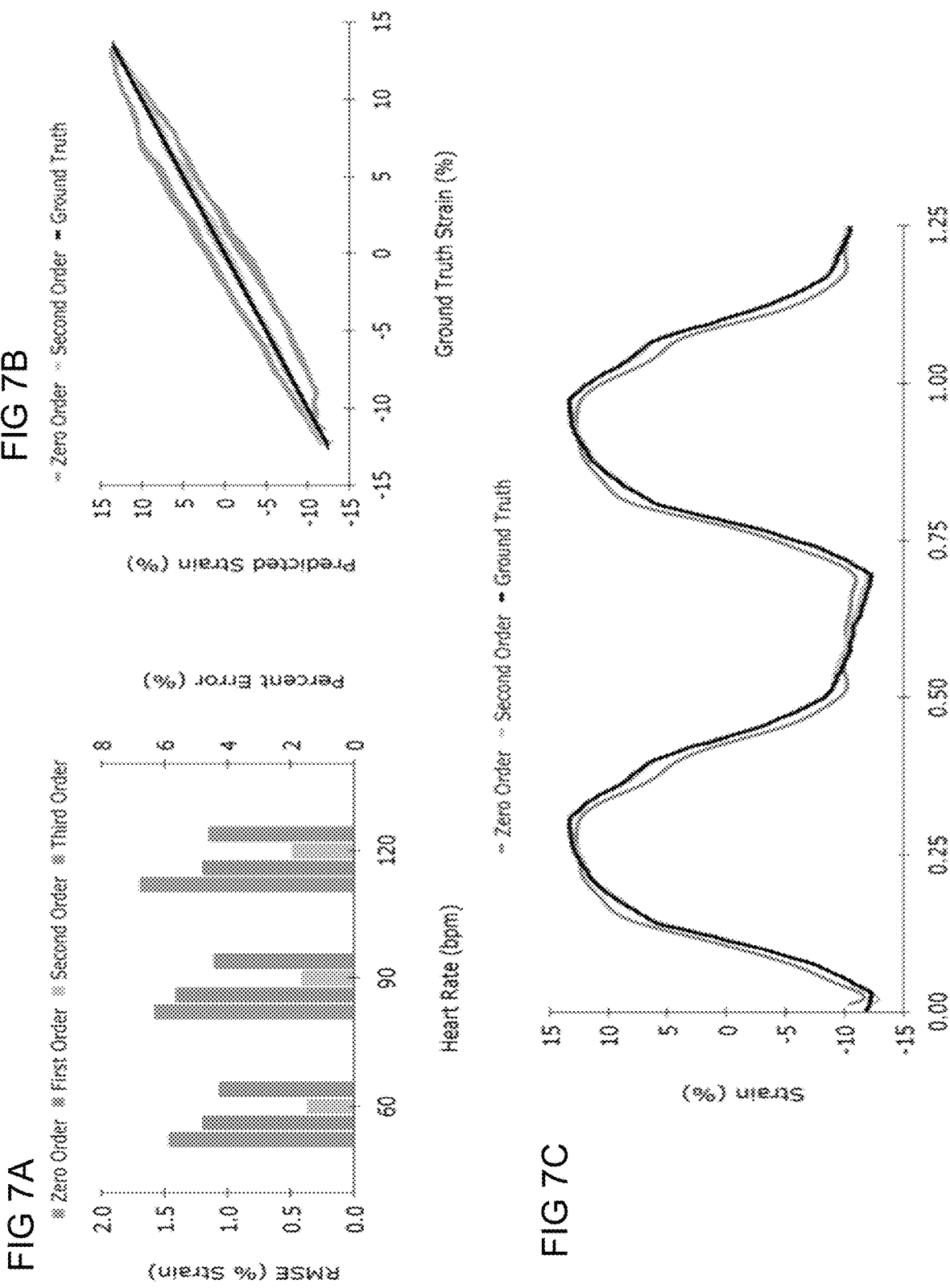
FIGS. 7A-C show application-specific model validation according to an exemplary embodiment of the invention.

FIG. 7A compares the errors in predicted strain between the zero, first, second, and third order models across a range of heartbeats. The second order model demonstrates a significant reduction in RMSE by 73%, averaged across all cases, whereas the first and second order models reduce error by 20% and 30%, respectively. Although results from the model fitting in Table 1 suggest that both the second and third order models will perform substantially better, the inability for the third order model to correctly predict the test data is likely due to overfitting, providing compelling evidence for the choice of the second order model. FIGS. 7B-C illustrate the response of the 90 bpm scenario for both second order and zero order (linear) mapping. The linear mapping shows clear hysteresis, and the second order TF compensates effectively.

Dynamic Curvature

The sensor's ability to conform to a heart-like surface and reliably measure strain over cyclic loading conditions was investigated in a benchtop setup. A ventricular phantom was modeled using a hollow prolate chamber design, which is a simple, widely used representation of ventricular geometry. A negative mold of the prolate was 3D printed and subsequently cast with silicone of shore hardness 00-20, corresponding to a Young's modulus comparable to that of the heart. The prolate was mounted to a custom rig with attached tubing to allow for inflation and deflation of the chamber with air.

Figures 8A, 8B:
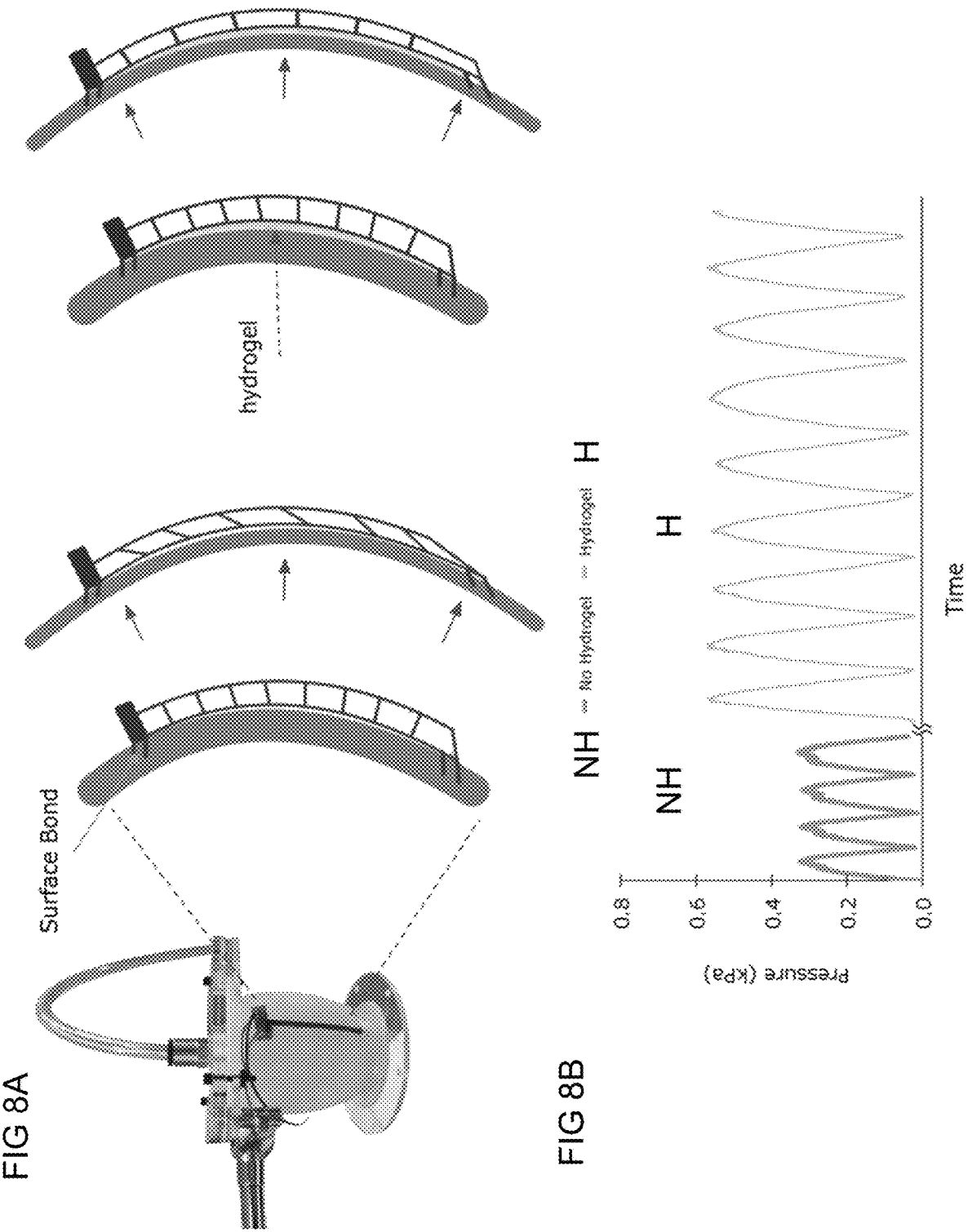
FIGS. 8A-B show strain sensor on a compliant, curved surface according to an exemplary embodiment of the invention.
Figure 9:
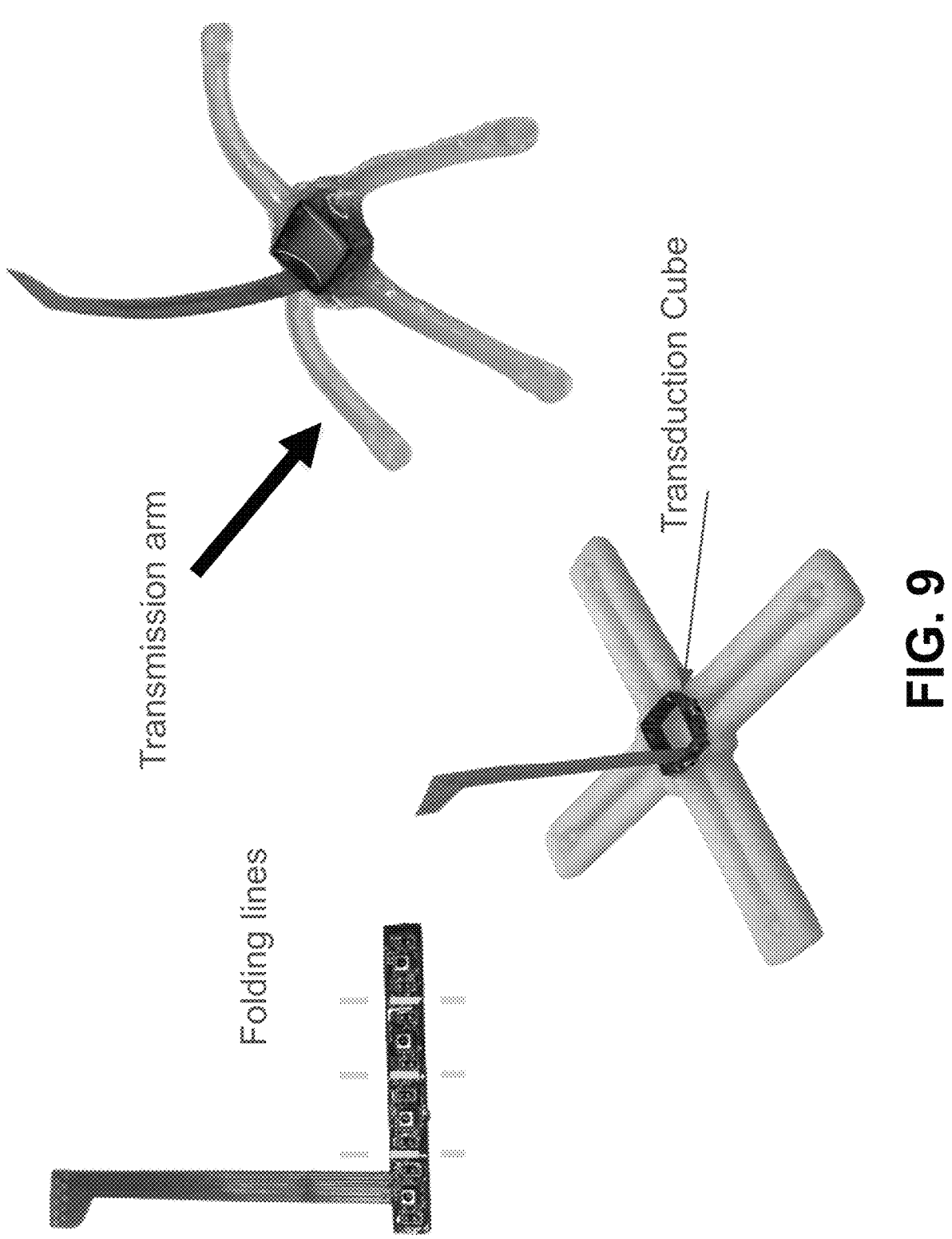
FIG. 9 shows according to an exemplary embodiment of the invention how the sensor technology can be expanded. Shown is a three-dimensional example of multiplexed flexible polymide circuits. Multiple transduction elements can be organized in a three-dimensional pattern or a cube (along the folding lines), and with that multiple transmission (sensing) elements, where each of the capacitive diaphragms of the multiple transduction elements is attached to the cross-sectional area of the end of the respective transmission element of the multiple transmission elements. As such in another example as a strain sensor for the heart, the multiple transmission elements are adapted in shape to confirm to shapes of a heart. An arm can be cast to the three-dimensional pattern or the cube, where the arm is cast a more or less perpendicular fashion to the three-dimensional pattern or the cube.
Figure 10:
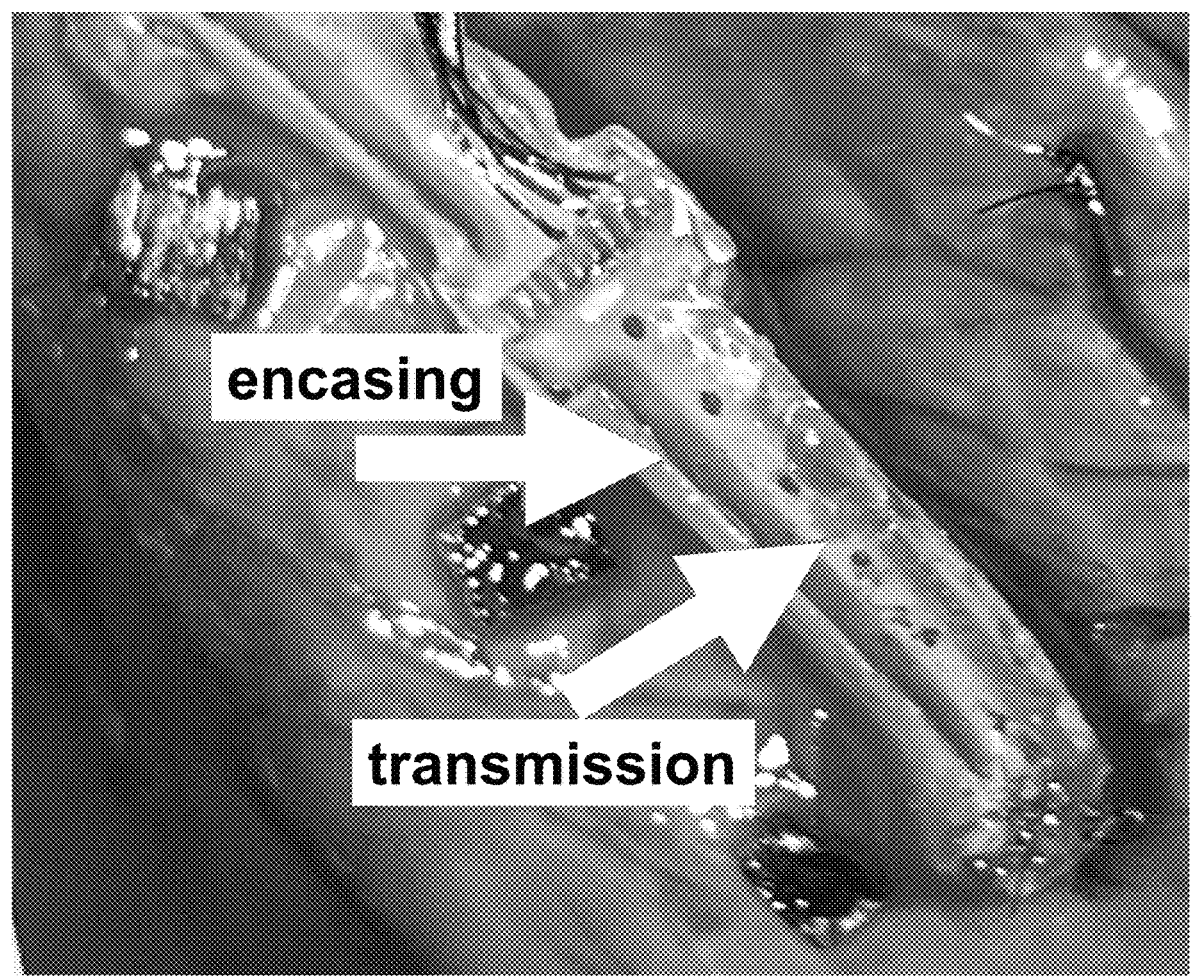
FIG. 10 shows according to an exemplary embodiment of the invention how the strain sensor can be applied to or adapted to the heart. In this example, the transmission element can be cast (encased) with a material that is at least four times less stiff or substantially less stiff than a material of the transmission element. The material of the cast can be a silicone gel at least four times or substantially less stiff than the material of the transmission element. In another example, the material of the cast is a silicone, a polyurethane, or a material with a Shore 000 hardness.

The sensor was bonded with adhesive to the phantom at two points, the PCB end and the tail end of the transmission element. FIG. 8A illustrates a critical mounting consideration for this application. To achieve efficient coupling between stretch and pressure on the diaphragm, it is necessary to ensure that the uniaxial stress is transmitted throughout the length of the stretchable element and not modified by counteracting forces or moments. In particular, frictional forces between the sensor and phantom surface can cause shear in the transmission element, attenuating the coupling between stretch and normal stress on the diaphragm in a complex manner (FIG. 8B, Left column). Note that this phenomenon is amplified in our experimental test set-up, as the silicone-cast phantom has a higher coefficient of friction than the surface of the heart. To alleviate frictional forces, a commercially available, biocompatible hydrogel (Silvex, USA) was spread between the phantom surface and the sensor. The left and right columns in FIG. 8B illustrate how friction can cause shear and affect pressure-strain coupling. Additionally, the inventors cast the PCB into a small anchoring sleeve that is rigidly bonded to the phantom to prevent rotation. The phantom was manually inflated and deflated with 70 mL of air, and the sensor signal was recorded for two cases, with and without hydrogel. The graph in FIG. 8B depicts the results, clearly showing that the friction-reducing hydrogel increases the signal, likely due to enhanced mechanical coupling between overall stretch of the elastic element and strain at the transducer.

What is claimed is:

1. A strain sensor, comprising:
(a) a transmission element, wherein the transmission element is an elongated homogeneous elastomer defining a width and a height of a cross-sectional area, a length and a Young's modulus of the elongated homogeneous elastomer; and
(b) a transduction element comprising a MEMS transducer with integrated signal processing and digital communication, wherein the MEMS transducer is a barometric pressure sensor with a capacitive diaphragm, wherein the capacitive diaphragm is attached to the cross-sectional area of an end of the transmission element,
such that the transmission element couples a mechanical signal of interest applied to an aspect of the transmission element to variations in stress onto the capacitive diaphragm, which is then converted into an electrical signal,
wherein the transmission element acts as a spring with a stiffness, and the transduction element acts as a deformation normal force sensor that is mechanically attached to the cross-sectional area of end of the transmission element, and wherein when the spring stretches, the normal force at the cross-sectional area of the end of the transmission element increases in proportion to the spring stiffness and that normal force is then transduced into the electrical signal.

2. The strain sensor as set forth in claim 1, wherein the transmission element is adapted in shape to conform to a shape of a heart.

3. The strain sensor as set forth in claim 1, further comprising multiple transduction elements organized in a three-dimensional pattern or a cube, and further comprising multiple transmission elements, wherein each of the capacitive diaphragms of the multiple transduction elements is attached to the cross-sectional area of the end of the respective transmission element of the multiple transmission elements.

4. The strain sensor as set forth in claim 3, wherein the multiple transmission elements are adapted in shape to conform to shapes of a heart.

5. The strain sensor as set forth in claim 3, further comprising an arm cast to the three-dimensional pattern or the cube, wherein the arm is cast in a more or less perpendicular fashion to the three-dimensional pattern or the cube.

6. The strain sensor as set forth in claim 1, wherein the transmission element is cast with a material that is at least four times less stiff or substantially less stiff than a material of the transmission element.

7. The strain sensor as set forth in claim 6, wherein the material of the cast is a silicone gel at least four times less stiff than the material of the transmission element.

8. The strain sensor as set forth in claim 6, wherein the material of the cast is a silicone, a polyurethane, or a material with a Shore 000 hardness.

9. The strain sensor as set forth in claim 1, wherein the length is in a range of 10 mm to 100 mm.

10. The strain sensor as set forth in claim 1, wherein the Young's modulus is in a range of 40 kPa to 500 kPa.

11. The strain sensor as set forth in claim 1, wherein the elongated homogeneous elastomer is made from silicone, polyurethane, sterene-isoprene- rubber, or natural rubber.

* * * * *